United States Patent
Iizuka et al.

(10) Patent No.: US 9,250,235 B2
(45) Date of Patent: Feb. 2, 2016

(54) TEST REAGENT, AND METHOD FOR MEASURING ANALYTE IN TEST SAMPLE USING SAME

(75) Inventors: Masayuki Iizuka, Gosen (JP); Mayumi Kano, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 1163 days.

(21) Appl. No.: 13/254,765

(22) PCT Filed: Mar. 4, 2010

(86) PCT No.: PCT/JP2010/053541
§ 371 (c)(1),
(2), (4) Date: Jan. 13, 2012

(87) PCT Pub. No.: WO2010/101213
PCT Pub. Date: Sep. 10, 2010

(65) Prior Publication Data
US 2012/0107957 A1    May 3, 2012

(30) Foreign Application Priority Data
Mar. 5, 2009   (JP) .................. 2009-051514

(51) Int. Cl.
G01N 33/546 (2006.01)
G01N 33/543 (2006.01)
(52) U.S. Cl.
CPC .... *G01N 33/54313* (2013.01); *G01N 33/54393* (2013.01)
(58) Field of Classification Search
None
See application file for complete search history.

(56) References Cited

U.S. PATENT DOCUMENTS

2009/0047685 A1    2/2009    Kohno et al.

FOREIGN PATENT DOCUMENTS

| EP | 0 064 275 A1 | 11/1982 |
|---|---|---|
| JP | 57-182168 A | 11/1982 |
| JP | 6-167495 A | 6/1994 |
| JP | 7-20129 A | 1/1995 |
| JP | 8-75746 A | 3/1996 |
| JP | 3095541 B2 | 10/2000 |

(Continued)

OTHER PUBLICATIONS

Extended European Search Report issued Oct. 4, 2012, in European Patent Application No. 10748806.6 0.

(Continued)

*Primary Examiner* — Chris L Chin
(74) *Attorney, Agent, or Firm* — Birch, Stewart, Kolasch & Birch, LLP

(57) ABSTRACT

Object: To provide a test reagent for the analyte in a test sample, utilizing the level of agglutination of a particle suspension which suspend insoluble carrier particles carrying a substance for capturing the analyte as an indicator, which reagent does not undergo self-agglutination during storage, and which non-specific agglutination rarely occurs during measurement, as well as to provide a method for the analyte to be measured in a test sample. Means for Solution: The test reagent for the analyte comprises at least a Solution A which is a buffer solution having an electric conductivity of not less than 30 ms/cm; and a Solution B having an electric conductivity of not more than 6.5 ms/cm, the Solution B being a particle suspension which suspends particles which are insoluble carrier particles carrying a substance for capturing the analyte.

14 Claims, 2 Drawing Sheets

(56) References Cited

FOREIGN PATENT DOCUMENTS

| | | |
|---|---|---|
| JP | 2005-351643 A | 12/2005 |
| WO | WO 2007/063616 A1 | 6/2007 |

OTHER PUBLICATIONS

Gallardo et al., "An experimental investigation of the stability of ethylcellulose latex Correlation between zeta potential and sedimentation," European Journal of Pharmaceutical Sciences (2006), vol. 26, pp. 170-175.

TEST REAGENT, AND METHOD FOR MEASURING ANALYTE IN TEST SAMPLE USING SAME

TECHNICAL FIELD

The present invention relates to a test reagent for measuring the analyte in a test sample, utilizing the level of agglutination by particle suspension which suspends insoluble carrier particles carrying a substance for capturing the analyte as an indicator, as well as to provide a method for measuring the analyte in a test sample using the above test reagent.

BACKGROUND ART

The method of measuring a substance to be measured (antigen or antibody) in a test sample, using a test reagent with particle suspension which suspends insoluble carrier particles carrying an antibody or antigen, utilizing the level of agglutination by the particles after reacting with the test sample as an indicator, is known as immunoagglutination and is widely used.

It has been reported that insoluble carrier carrying an antibody can be dispersed in a liquid phase with a low ionic strength having an NaCl concentration not higher than a prescribed concentration, or conversely, in a liquid phase with a high ionic strength having an NaCl concentration not lower than a prescribed concentration.

The insoluble carrier carrying a protein suspended in a solvent with a low ionic strength having a NaCl concentration not higher than a prescribed concentration, that is, suspended in a solvent having a low electric conductivity, is outstanding in effectively attaining good dispensability and sensitivity. However, non-specific agglutination may occur due to contamination of ions by impurities from biological samples.

It is known that interferences that influence the immunological reaction of the target substance exist in biological samples. To avoid the influence by the interferences of the immunological reaction, methods employing reagents with various additives have been widely used. For example, a method is known for using the reaction solution for detecting a target substance and the buffer solution, which is a second reagent containing an additive, for avoiding the influence from interferences. In many cases, the buffer solution has an electric conductivity (about 15 to 20 ms/cm) close to that of the saline. In measuring systems using an antibody suspended insoluble carrier under a condition of a low electric conductivity, non-specific agglutination may occur when the reaction solution is mixed with the buffer solution during the measurement.

In immunoagglutination or the like, various additives (for example, polyethylene glycol or guanidine) may be used in order to increase the sensitivity of the reagent. However, if an additive is used, the electric conductivity will increase, therefore non-specific agglutination may occur when the reaction solution is mixed with the buffer solution during the measurement.

On the other hand, in cases where an insoluble carrier carrying a protein suspended in a solvent having a high electric conductivity is used, self-agglutination does not occur in a short time, not within a several hours. However, self-agglutination takes place during long-term storage for several days or several months or more, so that the storage may not be attained.

PRIOR ART DOCUMENTS

Patent Documents

[Patent Document 1] JP 2005-351643 A
[Patent Document 2] JP 3095541 B
[Patent Document 3] JP 57-182168 A Non-Patent Documents

[Non-patent Document 1] J. Biomater. Sci. Polymer Edn, Vol. 10, No. 11, PP. 1093-1105 (1999)

SUMMARY OF THE INVENTION

Problems to be Solved by the Invention

An object of the present invention is to provide a test reagent for a substance to be measured in a test sample, utilizing the level of agglutination by a particle suspension which suspends insoluble carrier particles carrying a substance for capturing the substance to be measured as an indicator, where the reagent does not undergo self-agglutination during storage, and with which non-specific agglutination rarely occurs during measurement, as well as to provide a method of measuring the analyte in a test sample.

Means for Solving the Problems

The inventors intensively studied to discover that self-agglutination does not occur during storage condition and non-specific agglutination can be inhibited during measurement by constituting the test reagent in a binary solution system including a particle suspension and a buffer solution, also by making the particle suspension with lower electric conductivity than a specific value, and making the buffer solution with higher electric conductivity than a specific value which is higher than the buffer solution normally employed in test reagents, and by mixing the buffer solution and the particle suspension immediately before the start of the measuring operation, thereby completing the present invention.

That is, the present invention provides a test reagent for measuring an analyte, the reagent comprising at least a Solution A which is a buffer solution having an electric conductivity of not less than 30 ms/cm; and a Solution B having an electric conductivity of not more than 6.5 ms/cm, the Solution B being a particle suspension which suspends insoluble carrier particles carrying a substance for capturing the substance to be measured. The present invention also provides a method of measuring the analyte in a test sample using the above test reagent according to the present invention, the method comprising the steps of mixing the Solution A, the Solution B and the test sample; and measuring the level of agglutination of the particles in the obtained mixture, wherein at least the Solution A and the Solution B are mixed immediately before the start of the measuring operation.

Effects of the Invention

By the present invention, since self-agglutination does not occur during storage, and non-specific agglutination rarely occurs during measurement, the substance to be measured in a test sample can be measured accurately.

MODE FOR CARRYING OUT THE INVENTION

Figure 1:
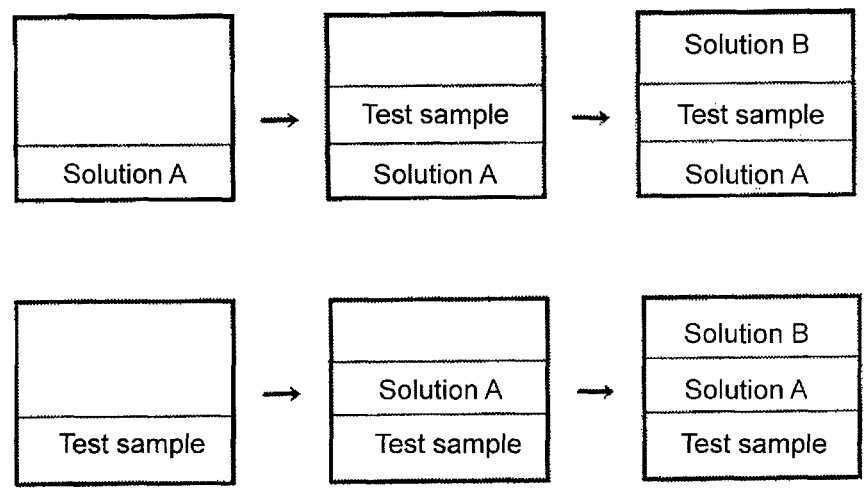
FIG. 1 shows a mode of the mixing method for mixing Solution A, Solution B and a test sample when the method of the present invention is carried out using an automatic measuring apparatus.

As described above, the reagent of the present invention comprises a Solution A, which is a buffer solution, and a Solution B, which is a particle suspension. The Solution A and the Solution B are two separate liquids contained in different containers. These solutions are mixed immediately before the measuring operation. The mode of mixing will be described later.

Solution A (Buffer Solution)

The buffering agent contained in Solution A, which is a buffer solution, may be a well-known buffering agent normally used in test reagents. Preferred examples of the buffering agent include amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine; salts of carboxylic acids such as citric acid, maleic acid and glutaric acid; phosphoric acid salts such as sodium phosphate and sodium hydrogen phosphate; carbonic acid salts such as calcium carbonate and magnesium carbonate; and Good's buffer. Tris buffer, Good's buffer, and phosphate buffers are preferably used, but the buffering agent is not restricted thereto.

The electric conductivity of Solution A is not less than 30 ms/cm, preferably not less than 35 ms/cm. There is no specific upper limit of the electric conductivity, and the electric conductivity is usually not more than 200 ms/cm, preferably not more than 100 ms/cm. By setting the electric conductivity of Solution A to not less than 30 ms/cm, non-specific agglutination during the measurement can be drastically inhibited. The buffer solutions widely used in the conventional test reagents are those having an electric conductivity similar to that of the saline, that is, those having an electric conductivity of about 15 to 20 ms/cm. Thus, one of the characteristic features of the present invention is to use a buffer solution having an electric conductivity higher than those of the buffer solutions normally used. The electric conductivity can be measured by a conventional method using a widely commercially available electric conductivity meter. The measurement of the electric conductivity is carried out at room temperature.

The electric conductivity of Solution A can be adjusted to an arbitrary value by adjusting the concentration of the above-described buffering agent, or by adding an aqueous ionic compound. Examples of the aqueous ionic compound include chlorides, bromide and iodides of alkaline metals such as sodium and potassium, and of alkaline earth metals such as magnesium and calcium, as well as carbonic acid salts, hydrogen carbonic acid salts, acetic acid salts and sulfuric acid salts containing these metals; and alums. Among these, NaCl is simple and preferred. By using a commercially available electric conductivity meter, the electric conductivity of a liquid can be measured in real-time, so that a desired electric conductivity can be easily attained by adding the aqueous ionic compound while measuring the electric conductivity.

Solution B (particle suspension) As described above, in Solution B, insoluble carrier particles carrying a substance for capturing the substance to be measured are contained in suspended state. The suspended particles are not restricted at all, and may be well-known particles conventionally used in test reagents.

More particularly, the substance for capturing the substance to be measured may be any substance as long as it can specifically bind to the substance to be measured, that is, a substance that can bind to the substance to be measured through a specific binding reaction such as antigen-antibody reaction or ligand-receptor reaction. The method wherein antigen-antibody reaction is utilized is a well-known immunoassay called immunoagglutination. In cases where the substance to be measured is an antigen, an antibody which undergoes antigen-antibody reaction with the antigen, or an antigen-binding fragment thereof (such as Fab fragment or $F(ab')_2$ fragment retaining the ability to bind with the antigen) is carried. Even in cases where the substance to be measured is an antibody, an antibody or an antigen-binding fragment thereof is carried because an antibody is also an antigen. The antibody may be either a monoclonal antibody or a polyclonal antibody.

In cases where the substance to be measured is an antigen, examples of the substance to be measured include, but are not limited to: protein markers such as CRP (C-reactive protein), prostate-specific antigen, ferritin, β-2 microglobulin, myoglobin, megalin, podocalyxin, transferrin, albumin and creatinine; various tumor markers; lipoproteins such as LDL, HDL and TG; viral antigens such as influenza A virus, influenza B virus, RS virus (RSV), rhinovirus, rotavirus, norovirus, adenovirus, astrovirus, HAV, HBs, HCV, HIV and EBV; antigens of bacteria such as Chlamydia trachomatis, hemolytic streptococcus, Bordetella pertussis, *Helicobacter pylori*, leptospire, Treponema pallidum, Toxoplasma gondii, Borrelia, Legionella, anthrax bacteria and MRSA; toxins produced by bacteria; mycoplasma lipid antigens; peptide hormones such as human chorionic gonadotropin; steroids such as steroid hormones; physiologically active amines such as epinephrine and morphine; vitamins such as vitamin Bs; prostaglandins; antibiotics such as tetracycline; agricultural chemicals; and environmental hormones. Preferred examples include antigens such as CRP, prostate-specific antigen, ferritin and β-2 microglobulin.

In cases where the substance to be measured is an antibody, examples include antibodies which specifically react with the antigen such as the above-described protein markers, various tumor markers, lipoproteins, viral antigens, bacterial antigens, toxins produced by bacteria or the like, peptide hormones, steroids, physiologically active amines, vitamins, antibiotics, agricultural chemicals and environmental hormones.

In cases where the analyte is an antigen, the carrier particles are sensitized with an antibody that binds to the analyte. In cases where the analyte is an antibody, the carrier particles are sensitized with an antigen that binds to the analyte. In cases where the analyte is a ligand, the carrier particles are sensitized with a receptor that binds to the analyte. In cases where the analyte is a receptor, the carrier particles are sensitized with a ligand that binds to the analyte.

The insoluble carrier may also be a well-known material that is conventionally used in test reagents. Examples thereof include resin latexes made of polyethylene or polystyrene; and particles of alumina, silica, gold colloid, magnetic particles and the like. Among these insoluble carriers, latex particles, especially polystyrene latex particles are preferably used.

The concentration of the suspended particles in Solution B may be appropriately selected depending on the type of the substance for capturing the analyte, the type of the analyte, the expected concentration of the analyte in the test sample and so on, and it is usually about 0.01 to 0.5%.

The electric conductivity of Solution B is not more than 6.5 ms/cm, preferably not more than 5 ms/cm. When the electric conductivity of Solution B is not more than 6.5 ms/cm, self-agglutination of the particles during the storage is prevented, and non-specific agglutination during the measurement rarely occurs. There is no specific lower limit of the electric conductivity, and the electric conductivity is usually not less than 0.1 ms/cm. The electric conductivity of not more than 6.5 ms/cm is attained by using water, an alcohol (e.g., ethanol or the like), sugar solution (e.g., glucose, sucrose, maltose, lactose) or the like as the solvent of Solution B. Sodium chloride or a buffering agent may be added to Solution B to the extent that the above-described electric conductivity can still be attained.

With the test reagent of the present invention, an additive(s) such as coloring reagents and reactive reagents for detecting the analyte; enzymes such as cholesterol oxidase and cholesterol esterase; surfactants; proteins for stabilizing antibody or inhibiting non-specific reactions; sugars and glycerol for adjusting the specific gravity may be co-employed. These additives may be added to Solution A or Solution B, or to another reagent (still another liquid) separate from Solution A and Solution B.

Measuring Method

The measuring method according to the present invention using the above test reagent comprises the steps of mixing Solution A, Solution B and the test sample; and measuring the level of agglutination of the above-described particles in the obtained mixture.

The test sample is not at all restricted as long as it may contain the above-described antigen, antibody or the like which is the analyte. Since, however, the non-specific agglutination during the measurement presumably stemmed from the contamination of the ions from the contaminants in the test sample, the present invention most exhibits its power when applied to a test sample collected from human or animal, preferably human body. Examples of such a test sample include liquids such as blood, serum, urine, spinal fluid, sweat, lymph fluid, saliva and gastric juice; feces; hair; corneum; and nail. Blood, serum or plasma originated from blood is especially preferably employed.

Figure 2:
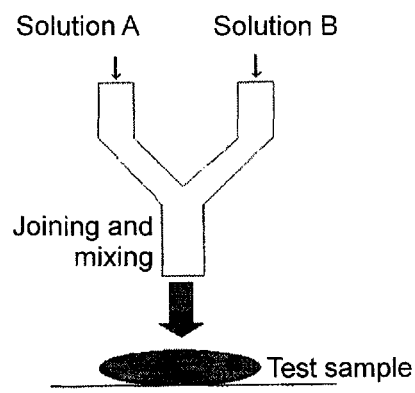
FIG. 2 shows another mode of the mixing method for mixing Solution A, Solution B and a test sample when the method of the present invention is carried out by an automatic measuring apparatus using a Y-shaped tube.
Figure 3:
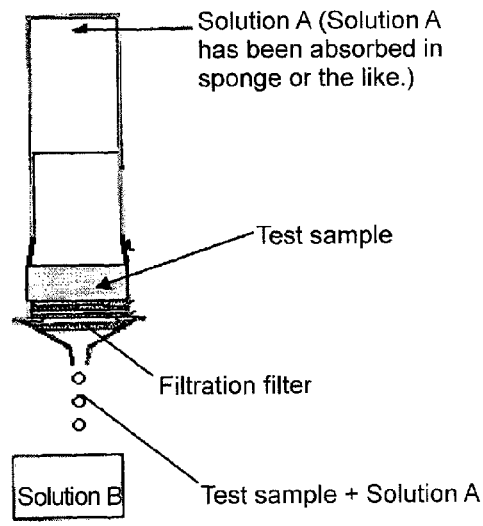
FIG. 3 shows another mode of the mixing method for mixing Solution A, Solution B and a test sample when the method of the present invention is carried out using a filtration filter.

Regarding the mixing of Solution A, Solution B and the test sample, the order of mixing is not restricted as long as these three (in cases where the test reagent includes a separate additive, also the additive) can be mixed. The mixing method includes a method wherein the three are simultaneously mixed; a method wherein the test sample is mixed after mixing Solution A and Solution B; a method wherein Solution B is mixed after mixing Solution A and the test sample; and so on. Agglutination method using an automatic measuring apparatus is also widely carried out, and a commercially available automatic measuring apparatus may preferably be employed in the present invention too. Embodiments of mixing Solution A, Solution B and the test sample using an automatic measuring apparatus include, for example, those shown in FIGS. 1 and 2. In the method shown in FIG. 1, the lower liquid is first added and the upper liquid is later added. The method shown in FIG. 2 is a method using a Y-shaped tube, wherein Solution A and Solution B are joined and mixed, and then the obtained mixture is mixed with the test sample. The method shown in FIG. 3 is a method using a filtration tube, wherein Solution A is placed in the tube, test sample is placed in the filter, Solution A and the test sample are subjected to mixing filtration, and the resulting mixture is dropped in Solution B. It is preferred to stir the mixture after the mixing.

At least the mixing of Solution A with Solution B is carried out immediately before the start of the measuring operation. The term "measuring operation" herein means the operation of measuring the degree of agglutination of the particles in the mixture, and is usually the measurement of absorbance or turbidity. The term "immediately before" herein means within 10 minutes, preferably within 5 minutes before the start of the measuring operation. By mixing Solution A with Solution B immediately before the start of the measuring operation, prevention of self-agglutination during storage and of the non-specific agglutination during the measurement can be attained. It is preferred to set the temperature of the respective liquids at the time of the mixing to the temperature at which the reaction is carried out, and usually from room temperature to 37° C.

After the mixing, reaction is carried out as in the conventional method usually for about 1 minute to 1 hour, preferably about 3 minutes to 15 minutes. The level of agglutination is measured in the same manner as in the conventional methods, usually by an optical method, preferably by measuring the absorbance or the turbidity. The analyte in the test sample can be measured by carrying out measurements for standard samples having various known concentrations; plotting the relationship between the concentration and the measured value (absorbance or the like) to prepare a calibration curve; and applying the measured value obtained for a test sample to the calibration curve. It is intended that the term "measurement" include any of detection, quantification and semi-quantification.

Test Reagent Kit

The test reagent kit of the present invention using the above test reagent of the present invention comprises chemicals and parts required for the test, such as Solution A, Solution B, containers and the like.

The present invention will now be described in more detail by way of an example. However, the present invention is not restricted to the example below.

EXAMPLES

Examples 1 to 3, Comparative Examples 1 to 5

The difference in the self-agglutination of the particle suspension (Solution B) which suspends the insoluble carrier particles carrying a protein was measured as described below. Using the saline as a blank sample, the difference in the non-specific agglutination under reaction conditions having varying electric conductivity of the buffer solution (Solution A) was evaluated. In addition, difference in the sensitivity was evaluated by measuring CRP.

Materials Used

Solution A: Sodium chloride was added to a buffer solution containing 100 mM Tris monitoring the electric conductivity to attain a prescribed electric conductivity.

Electric conductivity: 8 ms/cm (sodium chloride concentration: 50 mM, Comparative Examples 1 and 5); 16 ms/cm (sodium chloride concentration 150 mM, Comparative Example 2); 35 ms/cm (sodium chloride concentration: 400 mM, Example 1); 75 ms/cm (sodium chloride concentration: 1000 mM, Example 2, Comparative Examples 3 and 4), 200 ms/cm (sodium chloride concentration: 5000 mM, Example 3).

Solution B: Sodium chloride was added to a reaction solution that had 0.1% polystyrene latex with an average particle size of 220 nm carrying 0.25 mg/mL of anti-CRP antibody dispersed in the water to achieve the prescribed electric conductivity Electric conductivity: 5 ms/cm (sodium chloride: 50 mM, Examples 1 to 3, Comparative Examples 1 and 2), 15 ms/cm (sodium chloride: 150 mM, Comparative Example 3), 78 ms/cm (sodium chloride: 1000 mM, Comparative Examples 4 and 5).

Method

The initial absorbance and the absorbance at one month later of Solution B were measured to check the occurrence of self-agglutination.

The saline was used as a blank test sample, and the reagent obtained by mixing the above-described Solution A and Solution B was subjected to measurement using an automatic analyzer to check the non-specific agglutination of the reagent. More particularly, on HITACHI 7180 (trade name) automatic analyzer, 120 μL of Solution A was added to 2.4 μL of physiological saline; the obtained mixed liquid was stirred at 37° C.; the resulting mixture was left to stand for 5 minutes; 120 μL of the above-described Solution B was added; and the resulting mixture was further mixed with stirring at 37° C. The agglutination reaction after 5 minutes was measured as the change in absorbance at 570 nm.

Measurement of CRP was carried out by using a test sample solution containing 0.05 mg/dL of CRP, subjecting the reagent obtained by mixing the above-described Solution A and Solution B to measurement by the automatic analyzer to check the change in the absorbance. That is, on HITACHI 7180 (trade name) automatic analyzer, 120 μL of the above-described Solution A was added to 2.4 μL of 0.05 mg/dL CRP solution, the obtained mixed liquid was stirred at 37° C.; the resulting mixture was left to stand for 5 minutes; 120 μL of the above-described Solution B was added; and the resulting mixture was further mixed with stirring at 37° C. The agglutination reaction after 5 minutes was measured as the change in absorbance at 570 nm.

Evaluation Method

Regarding self-agglutination, the absorbances of 0.1% dispersed polystyrene latex particles and of Solution B before and after the storage were measured, and self-agglutination at the respective electric conductivities was evaluated in accordance with the evaluation criteria below.

Evaluation Criteria

Based on the absorbance of the dispersion of 0.1% polystyrene latex particles:

○: difference is 15% or less

X: difference is more than 15%

Non-specific agglutination during the measurement was evaluated based on the change in the absorbance of the saline, measured by an automatic analyzer, in accordance with the evaluation criteria below.

Evaluation Criteria

○: Change in absorbance ΔAbs times 10,000 is not more than 20

X: Change in absorbance ΔAbs times 10,000 is more than 20

Measurement of CRP

CRP was measured by calculating the difference between the change in absorbance of the saline, which is a blank test sample, and the change in absorbance of 0.05 mg/dL CRP solution, and comparing the sensitivity.

Measurement of Electric Conductivity

The electric conductivities of Solution A and Solution B were measured by using electric conductivity meter CM-60G produced by TOA ELECTRONICS LTD. (electrode: CT-57101B, temperature 25° C.).

Results

The results are shown in Table 1 below.

TABLE 1

| | Comparative example 1 | Comparative example 2 | Example 1 | Example 2 | Example 3 | Comparative example 3 | Comparative example 4 | Comparative example 5 |
|---|---|---|---|---|---|---|---|---|
| Electric conductivity of solution B (ms/cm) | 5 | | | | | 15 | 78 | |
| Absorbance (Abs.) Initial | 1.37 | | | | | 2.48 | 1.38 | |
| Difference in absorbance from latex dispersion (%) | +10% | | | | | +98% | +10% | |
| Absorbance (Abs.) 1 month later | 1.39 | | | | | 2.50 | 2.81 | |
| Difference in absorbance from latex dispersion (%) | +11% | | | | | +100% | +115% | |
| Judgement: self-agglutination o:no x:yes | o | | | | | x | x | |

TABLE 1-continued

|  | Comparative example 1 | Comparative example 2 | Example 1 | Example 2 | Example 3 | Comparative example 3 | Comparative example 4 | Comparative example 5 |
|---|---|---|---|---|---|---|---|---|
| Electric conductivity of solution A (ms/cm) | 8 | 16 | 35 | 75 | 200 | 75 | 75 | 8 |
| Change in absorbance during measurement of physiological saline ($\Delta$Abs. × 10000) | 443 | 2202 | 2 | −5 | −3 | 5 | −2 | 7 |
| Judgement: non-specific agglutination o: no x: yes | x | x | o | o | o | o | o | o |
| Change in absorbance during measurement of 0.05 mg/dL CRP solution ($\Delta$Abs. × 10000) | — | — | 1017 | 443 | 169 | 118 | 60 | 144 |
| Difference | — | — | 1019 | 448 | 166 | 123 | 58 | 151 |
| Final judgement o: good x: unacceptable | x | x | o | o | o | x | x | x |

As shown in Table 1, in Comparative Examples 3 to 5 wherein the electric conductivity of Solution B is higher than the range defined in the present invention, self-agglutination occurred after storing for 1 month (in Comparative Example 3, self-agglutination occurred immediately after mixing). In Comparative Examples 1 and 2 wherein the electric conductivity of Solution A is lower than the range defined in the present invention, the absorbance changed even when the saline was subjected to the measurement, that is, non-specific agglutination occurred.

With Examples 1 to 3 and Comparative Examples 3 to 5 wherein non-specific agglutination did not occur, the change in the absorbance when 0.05 mg/dL CRP solution was subjected to the measurement was compared. Examples 1 to 3 showed higher change in absorbance than Comparative Examples 3 to 5. In Example 2 and Comparative Example 5, the electric conductivities of Solution A and Solution B were set almost opposite to each other, so that the final electric conductivities were about the same. However, Example 2 wherein the electric conductivity was set lower in Solution B than in Solution A according to the present invention showed higher absorbance.

Thus, with the test reagent at least comprising of Solution A, which is a buffer solution having the electric conductivity defined in the present invention, and of Solution B and by the measuring method of the present invention, self-agglutination of the latex particles in Solution B can be prevented, hence achieving excellent stability during the storage. In addition, non-specific agglutination was prevented and a measurement with high sensitivity was attained.

Example 3

Preparation of Calibration Curve

Using the reagent of the Example 2, measurements were conducted using standard CRP solutions having various concentrations in the same manner as described above to perform calibration. The relationship between the obtained change in absorbance and the CRP concentration is shown in FIG. 4.

Figure 4:
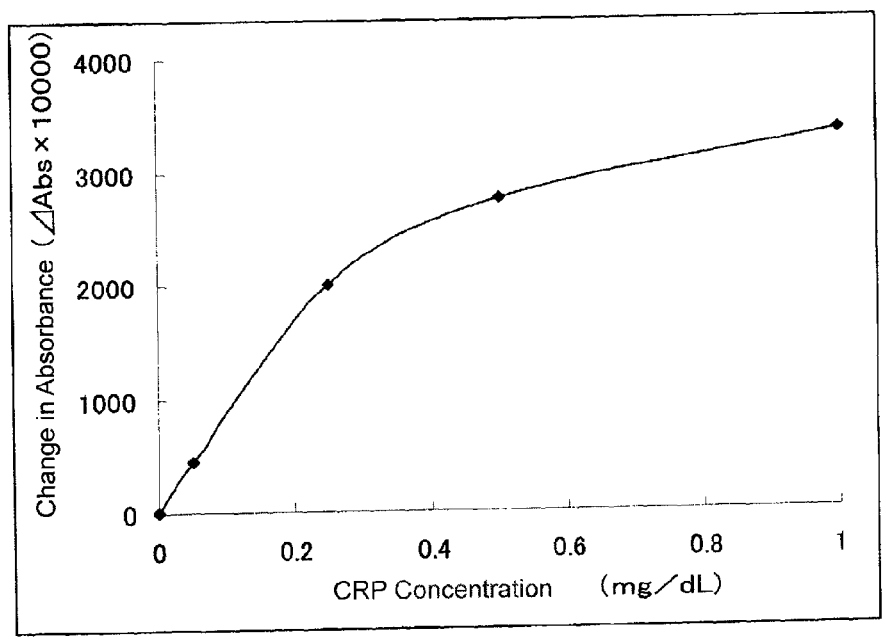
FIG. 4 shows a calibration curve prepared in an Example of the present invention.

As shown in FIG. 4, since the change in absorbance is depended on the CRP concentration, it was proved that CRP can be quantified using this reagent.

Example 4

Measurement of Serum Sample

Using the reagent of the Example 2, measurements of CRP were conducted for a serum sample in the same manner as described above. The measurements were repeated 20 times and the reproducibility was investigated. The results are shown in Table 2.

TABLE 2

| Measurement time | Absorbance |
|---|---|
| 1 | 0.101 |
| 2 | 0.101 |
| 3 | 0.105 |
| 4 | 0.101 |
| 5 | 0.103 |
| 6 | 0.102 |
| 7 | 0.104 |
| 8 | 0.103 |
| 9 | 0.101 |
| 10 | 0.103 |
| 11 | 0.102 |
| 12 | 0.105 |
| 13 | 0.104 |
| 14 | 0.104 |
| 15 | 0.103 |
| 16 | 0.105 |
| 17 | 0.101 |
| 18 | 0.105 |
| 19 | 0.102 |
| 20 | 0.101 |
| Mean | 0.103 |
| Standard deviation | 0.002 |
| CV | 1.50% |

As shown in Table 2, the measurement results show that the reproducibility of the actual serum sample, obtained by the method of the present invention, was very high.

The invention claimed is:

1. A method of preparing a test reagent for measuring an analyte, said method comprising:
mixing
1) a Solution A having an electric conductivity of not less than 30 ms/cm, said Solution A being a buffer solution, and
2) a Solution B having an electric conductivity of not more than 6.5 ms/cm, said Solution B being a particle suspension which suspends insoluble carrier particles carrying thereon a substance for capturing the analyte.

2. The method according to claim 1, wherein said Solution A has an electric conductivity of not more than 200 ms/cm.

3. The method according to claim 1 or 2, wherein said substance for capturing the substance to be measured is an antibody or an antigen-binding fragment thereof, or an antigen.

4. The method according to claim 1, wherein said insoluble carrier particles are latex particles.

5. The method according to claim 4, wherein said latex particles are polystyrene latex particles.

6. A method of measuring an analyte in a test sample, said method comprising:
mixing
a Solution A having an electric conductivity of not less than 30 ms/cm, said Solution A being a buffer solution,
a Solution B having an electric conductivity of not more than 6.5 ms/cm, said Solution B being a particle suspension which suspends insoluble carrier particles carrying thereon a substance for capturing the analyte, and
said test sample; and
measuring the analyte in the test sample by the level of agglutination of the particles in the obtained mixture;
wherein at least said Solution A and said Solution B are mixed immediately before the start of the measuring operation.

7. The measuring method according to claim 6, wherein said test sample is urine, spinal fluid or feces.

8. The measuring method according to claim 6, wherein said test sample is blood, serum or blood plasma.

9. A test reagent kit comprising a Solution A having an electric conductivity of not less than 30 ms/cm, said Solution A being a buffer solution; and a Solution B having an electric conductivity of not more than 6.5 ms/cm, said Solution B being a particle suspension which suspends insoluble carrier particles carrying thereon a substance for capturing the analyte.

10. The test reagent kit according to claim 9, wherein said Solution A has an electric conductivity of not more than 200 ms/cm.

11. The test reagent kit according to claim 9, wherein said substance for capturing the substance to be measured is an antibody or an antigen-binding fragment thereof, or an antigen.

12. The test reagent kit according to claim 9, wherein said insoluble carrier particles are latex particles.

13. The test reagent kit according to claim 12, wherein said latex particles are polystyrene latex particles.

14. A test reagent for measuring an analyte, said test reagent obtained by the method according to claim 1.

* * * * *